United States Patent [19]

Saeki et al.

[11] Patent Number: 5,639,601

[45] Date of Patent: Jun. 17, 1997

[54] SYNTHETIC PEPTIDE SEQUENCES USEFUL IN DETECTION OF FOOT AND MOUTH DISEASE

[75] Inventors: Takakiyo Saeki, Kodaira; Kenichi Sakamoto, Sagamihara, both of Japan

[73] Assignee: Director of the National Institute of Animal Health, Tsukuba, Japan

[21] Appl. No.: 630,897

[22] Filed: Apr. 4, 1996

[30] Foreign Application Priority Data

May 24, 1995 [JP] Japan ................... 7-148364

[51] Int. Cl.$^6$ .................. C12Q 1/70; G01N 33/53; G01N 33/546; A61K 38/00

[52] U.S. Cl. ............... 435/5; 435/7.1; 435/7.92; 435/7.94; 436/533; 530/300; 530/326; 530/327; 530/334

[58] Field of Search ............ 435/5, 7.1, 7.92, 435/7.94; 436/533; 530/300, 326, 327, 334

[56] References Cited

U.S. PATENT DOCUMENTS

| | | | |
|---|---|---|---|
| 4,493,795 | 1/1985 | Nestor, Jr. et al. | 530/326 |
| 4,683,136 | 7/1987 | Milich et al. | 424/189.1 |
| 4,859,765 | 8/1989 | Nestor, Jr. et al. | 530/333 |
| 5,019,383 | 5/1991 | Hopp | 424/194.1 |

OTHER PUBLICATIONS

Carroll et al, 1984, Nucleic Acid Research, vol. 12 pp. 2461–2472.
Ruppert et al, 1994, Vaccine, vol. 12, No. 6, pp. 492–498.
Kurz et al., 1981, Nucleic Acid Research, vol. 9, No. 8 pp. 1919–1931.
Bittle et al., 1982, Nature, vol. 298, pp. 30–33.
DiMarchi et al., 1986, Science, vol. 232, pp. 639–641.

Primary Examiner—Mary E. Mosher
Assistant Examiner—Ali R. Salimi
Attorney, Agent, or Firm—Oblon, Spivak, McClelland, Maier & Neustadt, P.C.

[57] ABSTRACT

Disclosed are peptides A and B for diagnosis of foot and mouth disease (FMD), having the amino acid sequences of Sequence Nos. 1 and 2, respectively, in Sequence Listing, and also antigens A and B for diagnosis of FMD each as bonded to a carrier. The peptides and antigens are usable for diagnosis of FMD in various FMD-infected animals, at high sensitivity and high specificity. Using these, rapid and easy diagnose of FMD is possible.

8 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Arg  Ser  Thr  Pro  Glu  Asp  Leu  Glu  Arg  Ala  Glu  Lys  Gln
 1                  5                              10
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 12
        ( D ) OTHER INFORMATION: /product="Serine or Glycine"

( x i ) SEQUENCE DESCRIPTION: SEQ ID NO:2:

```
Leu  Glu  Lys  Gln  Arg  Asp  Leu  Asn  Asp  Pro  Ser  Xaa  Lys  Tyr  Lys  Glu
 1                  5                              10                         15
Ala  Lys  Glu
```

SYNTHETIC PEPTIDE SEQUENCES USEFUL IN DETECTION OF FOOT AND MOUTH DISEASE

FIELD OF THE INVENTION

The present invention relates to peptides for diagnosis of foot-and-mouth disease and to antigens containing the peptide for diagnosis of foot-and-mouth disease and, more precisely, relates to such peptides and antigens utilizable for diagnosis of an international epizootic foot-and-mouth disease which is worldwide the most dangerous.

BACKGROUND OF THE INVENTION

Foot-and-mouth disease is a dangerous, international epizootic disease which causes the most serious injury to livestock. This is widely prevailing all over the world, for example, in Asia, middle East, Africa and South America except only some regions. Fortunately, at present, it is free in Japan. However, if once invaded, the eradication of the disease will be difficult since it is extremely strongly infectious, and if the worst comes to the worst, the disease will prove to be the deathblow to the internal livestock industry.

Foot-and-mouth disease (FMD) is a viral infectious disease, and the FMD virus causing the disease includes seven serotypes while the existence of more than 60 subtypes of the virus is known. The blood of the animal as infected with such FMD viruses shall have antibodies to the virus-constituting proteins, which are produced in the blood in accordance with numerous different types of viral mutation. Therefore, when the presence or absence of the FMD viral infection is diagnosed (judged) in animals, it is often impossible to serologically detect FMD viruses of different serotypes.

On the other hand, the FMD virus comprises a number of non-structural proteins such as typically RNA-dependent RNA polymerase which produces its own gene, and many of such non-structural proteins are common to all serotypes of FMD viruses. When a recent new vaccine as purified to a high degree is administered to an animal, almost no antibody to non-structural proteins is produced in the blood of the animal but, in fact, the existence of the antibodies to non-structural proteins in the blood of the FMD-infected animal is significantly recognized.

For these reasons, in order to diagnose the presence or absence of infection with FMD viruses in animals, it is considered extremely important to detect the antibodies specific to the non-structural proteins (3D;RNA polymerase, 3C;protease, L;protease, and other 2A, 2B, 2C, 3A and 3B proteins) existing in the blood samples collected from the animals to be tested.

Up to this time, various methods for diagnosis of FMD viral infections using, as the antigen the RNA polymerase site of 3D protein have been attempted by many scientists.

However, in the reaction systems having a relatively high detection sensitivity, such as enzyme-linked immunosorbent assay systems (ELISA), if the site having an amino acid sequence significantly common to that among Picornavirus which is close related to FMD virus is used as the antigen non-specific reactions often occur problematically.

In addition, it is said in the reports that have heretofore been made, that the reactivity of the 3D protein site with infected positive sera is not so good.

Given the situation, if a high-sensitivity method of detecting antibodies specific to only non-structural proteins, while being not accompanied by any non-specific reactions, is developed, it becomes possible to easily select and differentiate naturally-infected, antibody-positive animals from the group of vaccine-dosed, antibody-positive animals. Accordingly, it will be possible to provide a means of preventing FMD from invading FMD-free countries such as Japan and also to provide for FMD-infected countries an extremely valuable technique of applying vaccines to animals to thereby reduce the FMD-infected regions in the countries and even an extremely valuable technique of diagnosis of FMD in animals to thereby exterminate FMD in the FMD-infected countries.

SUMMARY OF THE INVENTION

Specifically, the first aspect of the present invention is to provide peptide A for diagnosis of FMD, having the amino acid sequence of Sequence No. 1 in Sequence Listing mentioned hereinunder.

The second aspect of the invention is to provide antigen A for diagnosis of FMD, containing peptide A as bonded to a carrier.

As one embodiment of the second aspect of the invention, the carrier comprises equine globulin or latex particles.

The third aspect of the invention is to provide a method for diagnosis of FMD where antigen A is used.

The fourth aspect of the invention is to provide peptide B for diagnosis of FMD, having the amino acid sequence of Sequence No. 2 in Sequence Listing mentioned hereinunder.

The fifth aspect of the invention is to provide antigen B for diagnosis of FMD, containing peptide B as bonded to a carrier.

As one embodiment of the fifth aspect of the invention, the carrier comprises equine globulin or latex particles.

The sixth aspect of the invention is to provide a method for diagnosis of FMD where antigen B is used.

DETAILED DESCRIPTION OF THE INVENTION

Figure 1:
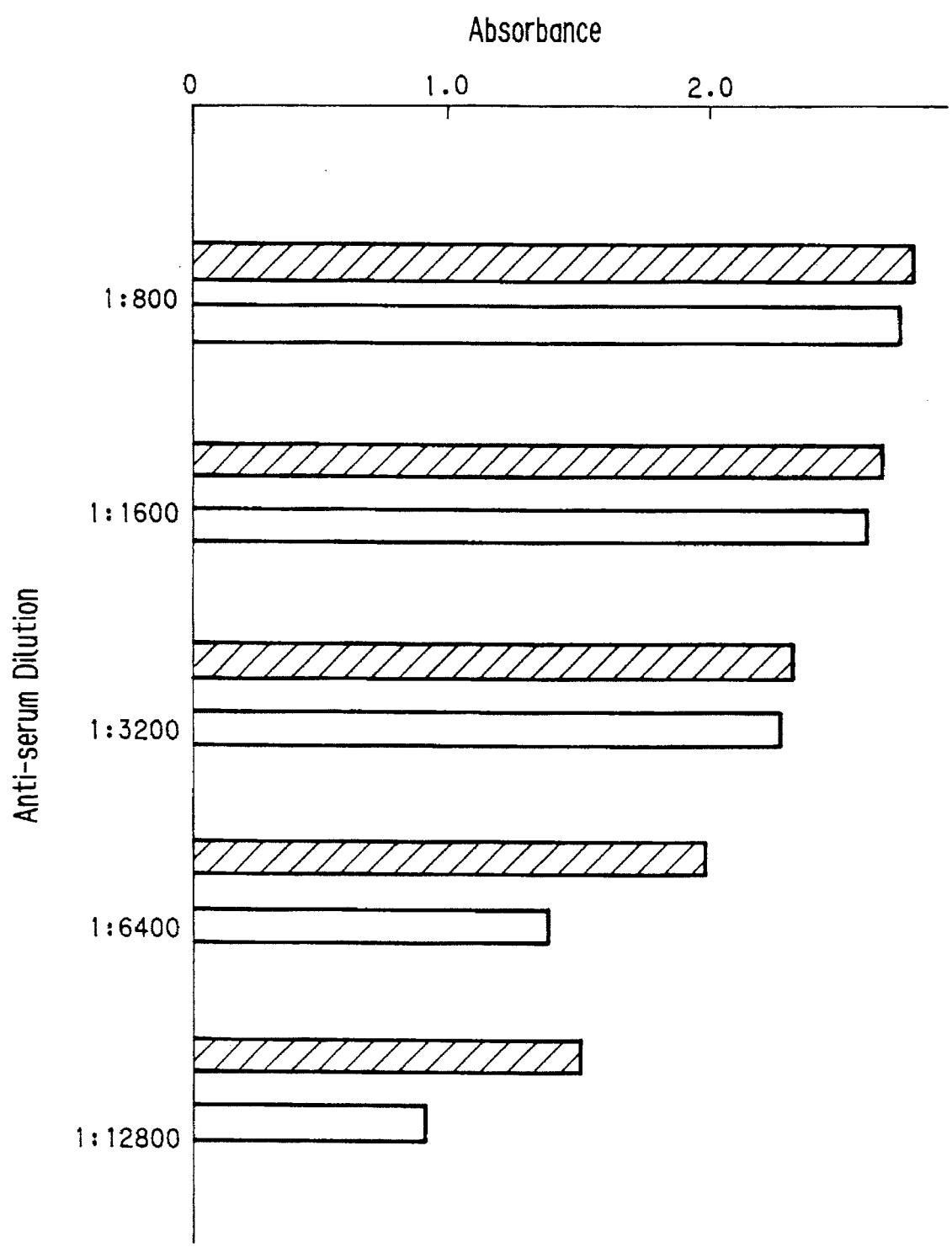
FIG. 1 shows the reactivity of antigen A and B with FMD-positive bovine sera collected 4 weeks after the FMD infection.

We, the present inventors, have produced as various peptide fragments, a part of the amino acid sequences of non-structural proteins which are common to different serotypes of FMD but they are different from close related Picornavirus. Then, in order to find out therefrom excellent antigen sites which has high specificity and has high reactivity, we have applied these peptides to various FMD-infected bovine sera to thereby evaluate and investigate as to whether or not these peptides are usable in diagnosis of the presence or absence of FMD-viral infection in cattle.

As a result, we have found peptide A and peptide B usable in diagnosis of FMD. In addition, we have further investigated the direct use of the peptide itself as the antigen and the use of the peptide as bonded to a carrier protein (e.g., globulin, albumin or the like in plasma) by covalent bonding also as the antigen, and have found that the antigen reactivity of the latter peptide as bonded to a carrier protein is higher than the former peptide itself. On the basis of these findings, we, the present inventors have completed the present invention.

The present invention provides a peptide A for diagnosis of FMD, having the amino acid sequence of Sequence No. 1 in Sequence Listing.

The present invention provides an antigen A for diagnosis of FMD, containing the peptide A as bonded to a carrier.

Further, the present invention relates to a method for diagnosis of FMD where the antigen A is used.

The present invention provides a peptide B for diagnosis of FMD, having the amino acid sequence of Sequence No. 2 in Sequence Listing.

The present invention provides an antigen B for diagnosis of FMD, containing the peptide B as bonded to a carrier.

Further, the present invention provides a method for diagnosis of FMD where the antigen B is used.

The present invention is described in detail hereinunder.

(1) Preparation of Peptide Samples:

According to computery retrieval of reference data, amino acid sequence sites each composed of about fifty, relatively hydrophilic amino acids were selected, which are common to FMD viruses while having a few parts common to other close related viruses and are considered to be easily recognized as antigens by individual animals, and these were produced by solid-phase chemical synthesis. Thus were obtained peptide samples each comprised of about 10 to 20 or more amino acid and corresponding to the site derived from any of all non-structural proteins (3D;RNA polymerase, 3C;protease, L;protease, and other 2A, 2B, 2C, 3A and 3B proteins).

(2) Evaluation and Examination of Peptide Samples:

The reactivity of each peptide sample was determined by an indirect ELISA technique using a bovine serum as obtained by experimental infection with FMD viruses, in which the peptide sample itself was directly used as the antigen or a combination of the peptide sample as bonded to a carrier protein by covalent bonding was used as the antigen. As the positive control, used was a partially purified native 3D protein.

(3) Selection of Peptides Usable in FMD Diagnosis:

Of the peptide samples prepared above, the peptide having the amino acid sequence of Sequence No. 1 in Sequence List was proved to be extremely strongly reactive with the antibody in FMD-infected animals. This peptide is referred to as peptide A for diagnosis of FMD. The sequence of this peptide is common to FMD viruses and probably is considered to construct a single epitope antigen. Therefore, the specificity of this peptide is expected to be extremely high.

On the other hand, another peptide was found to be usable in diagnosis of FMD, although its reactivity is somewhat lower than the reactivity of peptide A. This is referred to as peptide B for diagnose of FMD. Peptide B has the amino acid sequence of Sequence No. 2 in Sequence List, in which the 11th amino acid is either serine or glycine.

(4) Preparation of Antigens for Diagnosis of FMD:

The peptide for diagnosis of FMD was bonded to a carrier selected from various proteins and latex particles by covalent bonding to prepare an antigen for diagnosis of FMD.

Proteins usable for this purpose include albumin, globulin, hemocyanine, etc. Of these, especially preferred is equine globulin.

As latex particles that can be bonded to the peptide for diagnosis of FMD by covalent bonding, mentioned are particles of carboxylated polystyrene, etc.

(5) Evaluation and Selection of Antigens for Diagnosis of FMD:

The antibody titer of each antigen for diagnosis of FMD was determined by an indirect ELISA technique using a bovine serum as obtained by experimental infection with FMD viruses. As the control, used was a native FMD virus 3D protein.

As a result, it was found that peptide A and peptide B each as bonded to equine globulin exhibit a much higher antibody titer than the native 3D protein. Thus, peptide A and peptide B each as bonded to equine globulin were proved to be usable as the antigen for diagnosis of FMD.

Where the antigens thus prepared are used in diagnosis of FMD, various methods are employable. For example, employable are techniques of indirect ELISA, time-resolved fluorometric analysis, latex agglutination, etc. Since the last technique does not require any equipment with complicated, high-priced metering instruments, rapid and easy diagnosis of FMD with the antigens is possible, especially in field use. In addition, as the peptides themselves are extremely stable, they can be utilized even in the tropical and semitropical zones.

The method of the present invention is utilizable in diagnosis of FMD for various animals that may suffer from FMD, such as cattle, pigs, sheep, goats, buffalo, deer, elephants, etc.

As has been described in detail hereinabove, the present invention provides peptides and antigens for diagnosis of FMD, with which various animals as infected with FMD can be examined at high sensitivity and high specificity. Therefore, these peptides and antigens can be utilized for rapid and easy diagnosis of FMD infection, and the present invention contributes to diagnosis and prevention of FMD.

The present invention is described in more detail by means of the following examples, which, however, are not intended to restrict the scope of the present invention.

EXAMPLE 1

Peptides each having the amino acid sequence of Sequence No. 1 or 2 in Sequence List were produced according to the solid-phase Fmoc-peptide synthesizing method [see Atherton, E. et al.; A Mild Procedure for Solid-Phase Peptide Synthesis—Use of Fluorenylmethyloxycarbonyl Amino Acids, J. Chem. Soc. Chem. Commun., 13, 539–540 (1978)]. To synthesize these, used were Fmoc-L-protected amino acids (product of Nova in Switzerland) and special-grade chemicals (product of Kanto Chemical Co. or Nakarai Chemical Co.) as other general reagents.

Concretely, protected amino acids were bonded one after another to the amino-terminal side of the amino acid-resin compound, said amino-terminal is connected to the carboxyl terminal of the intended peptide by dehydro-condensation with dicyclohexyl carbodiimide (DCC) [see Chang, C. D. & Meienhofer, J.; Solid-Phase Peptide Synthesis Using Mild Base Cleavage of N-Alpha-Fluorenylmethyloxycarbonyl Amino Acids, Exemplified by a Synthesis of Dihydrosomatostation, Int. J. Peptide Protein Res., 11, 246–249 (1978)], which was repeated until the completion of the intended peptide. Every bonding of a new protected amino acid to the amino-terminal side was conducted in such a way that the presence or absence of any free amino acid in the peptide being synthesized was checked at every reaction stage and, if the presence of any amino acid was detected therein, the necessary reaction was repeated plural times until the confirmation of the absence of any non-reacted free amino acid in the peptide being synthesized and before the introduction of the new protected amino acid thereinto. This is to attain the complete reaction to synthesize the intended peptide.

Finally, after the intended, whole-length peptide was synthesized, the bonding of all the side-chain-protecting groups and the resin to the peptide was cut with trifluoroacetic acid (TFA) under presence of scavengers. Of the Fmoc-L-protected amino acids, an easily removable Pmc group was used as the guanidino-protecting group of arginine.

The peptide from which the resin had been cut was filtered through a glass filter, then TFA was removed therefrom with a vacuum evaporator, and the resulting crude peptide was washed several times with cold ether to remove therefrom the decomposates such as the side-chain-protecting groups, then dissolved in a small amount of acetic acid and freeze-dried.

EXAMPLE 2

This is to evaluate the reactivity of the peptides synthesized in Example 1 according to an indirect ELISA method using bovine sera as obtained by experimental infection with O-type FMD viruses. As the control negative sets, used were before-infected ones. The indirect ELISA method employed herein is as follows: The serum to be tested was diluted to a predetermined dilution, added to a plate as coated with a peptide to be the antigen or with a peptide-bonded antigen, and incubated at 37° C. for 1 hour. After this, the non-bonded antibody was completely removed by full washing, then a second antibody of anti-bovine peroxidase conjugate was added to the plate and further incubated for 1 hour at the same temperature, and the non-bonded second antibody was removed completely by washing. After this, a substrate was added to the plate to color it for colorimetry.

As the plate, used was Immunoplate MAXISORP (product of Nunc Co. in Denmark). As the anti-bovine peroxidase conjugate, used was anti-bovine IgG goat IG peroxidase (product of Kirregaard & Perry Lab. Inc. in U.S.A.).

A natural antigen as the positive control was prepared by partially purified O-type FMD virus infected BHK-21 cells derived from the kidney of a baby hamster. This antigen was tested according to the ELISA method, which revealed that the antigen is usable at a dilution of 1/200 or less. This gave a clear precipitation line by agar gel-diffusion method with a 1:16 dilution animal serum infected with a hetero-type, FMD virus Asia-1 type.

EXAMPLE 3

30 mg of equine globulin (product of Sigma in U.S.A.) was dissolved in 2 ml of a phosphate buffer. After having been dialyzed, this was put in about 500 ml of a phosphate buffer containing 0.7% glutaraldehyde for 30 minutes to thereby make it activated. Next, from 10 to 20 mg of the peptide synthesized in Example 1 was added thereto and reacted at room temperature for 4 hours. Then, an excessive amount of lysine hydrochloride was added thereto, by which the reaction was neutralized. Again this was dialyzed, and then the glutaraldehyde was completely removed therefrom. After having been freeze-dried, about 35 mg of equine globulin-bonded peptide was obtained.

EXAMPLE 4

Antigens A and B for diagnosis of FMD that had been prepared in the same manner as in Example 2 were used herein to check their reactivity with the serum as collected from a FMD-infected cattle (#4) 4 weeks after the infection. Precisely, the serum was diluted from 1:800 to 1:12800 by double stepwise dilution, and each serum dilution was applied to each antigen according to the above-mentioned indirect ELISA method. The results obtained are shown in FIG. 1.

As is obvious from FIG. 1, the reactivity of these antigens A and B with every serum dilution was extremely high while the reactivity of antigen A was higher than that of antigen B with the decrease in the concentration of the antigens. As opposed to these antigens A and B, the reactivity of the control, natural 3D protein antigen with the 1:800 serum dilution was not higher than 0.01.

EXAMPLE 5

Figure 2:
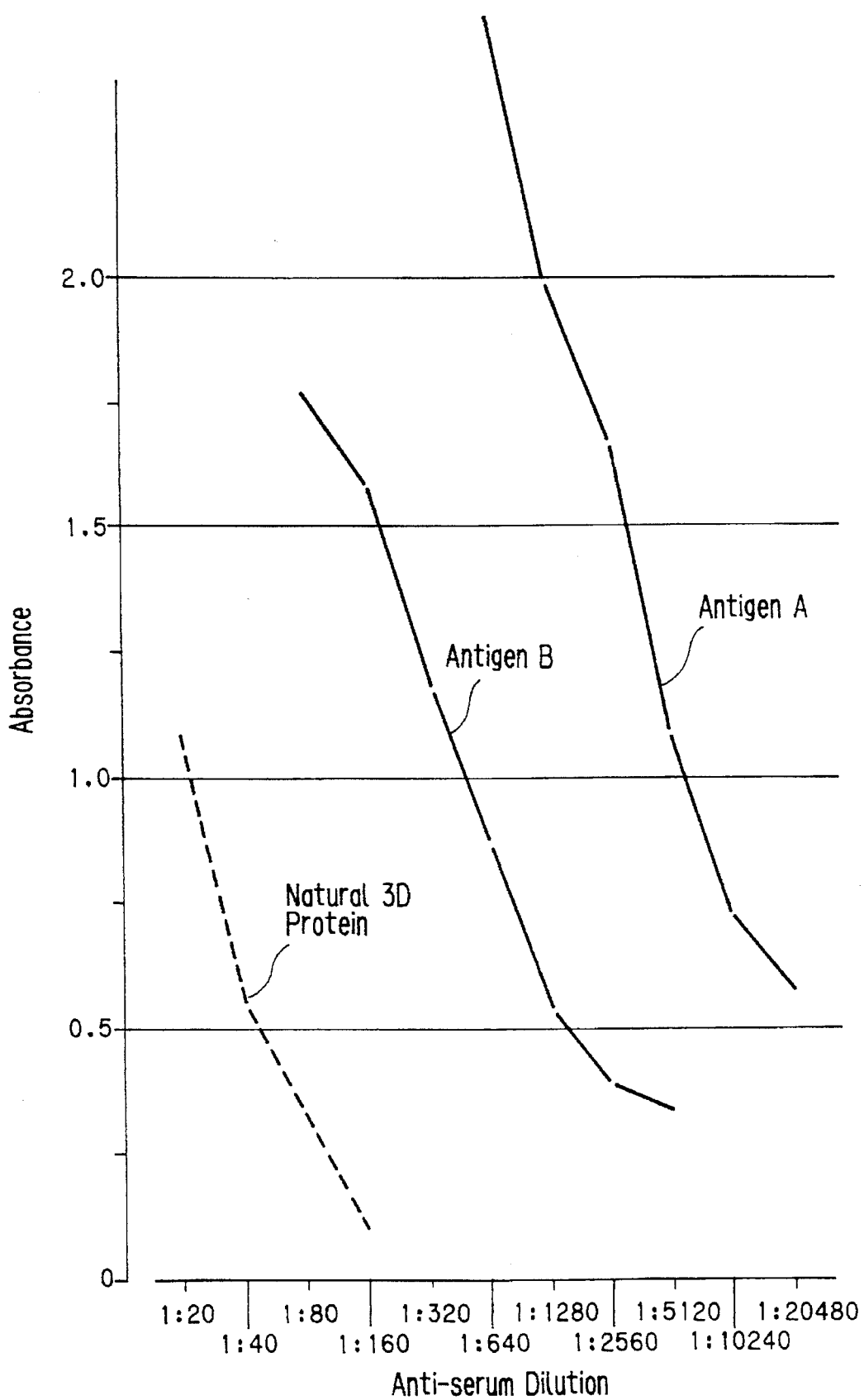
FIG. 2 shows the reactivity of antigen A and B with FMD-positive bovine sera collected 9 weeks after the FMD infection.

Antigens A and B for diagnosis of FMD that had been prepared in the same manner as in Example 2 were used herein to check their reactivity with the serum as collected from a FMD-infected cattle (#3) 9 weeks after the infection, according to the indirect ELISA method. The results obtained are shown in FIG. 2. As the control, used was the natural 3D protein.

As in FIG. 2, the positive control, natural 3D protein applied to the 1:20 serum dilution showed an absorbance of about 1.15 and that applied to the 1:40 serum dilution showed an absorbance of about 0.55. Though not shown, two equine globulin-bonded 3D protein partial peptide antigens gave almost the same results as those in FIG. 2.

FIG. 2 reveals that antigens A and B both have extremely high reactivity with the sera. In particular, it is noted that the reactivity of antigen A is extremely high or is several thousands times as much as that of the control, natural 3D protein.

However, equine globulin-bonded peptide antigens that had been prepared from the other peptide samples obtained in Example 1 in the same manner as in Example 3 did not show such high reactivity with the sera.

EXAMPLE 6

Figure 3:
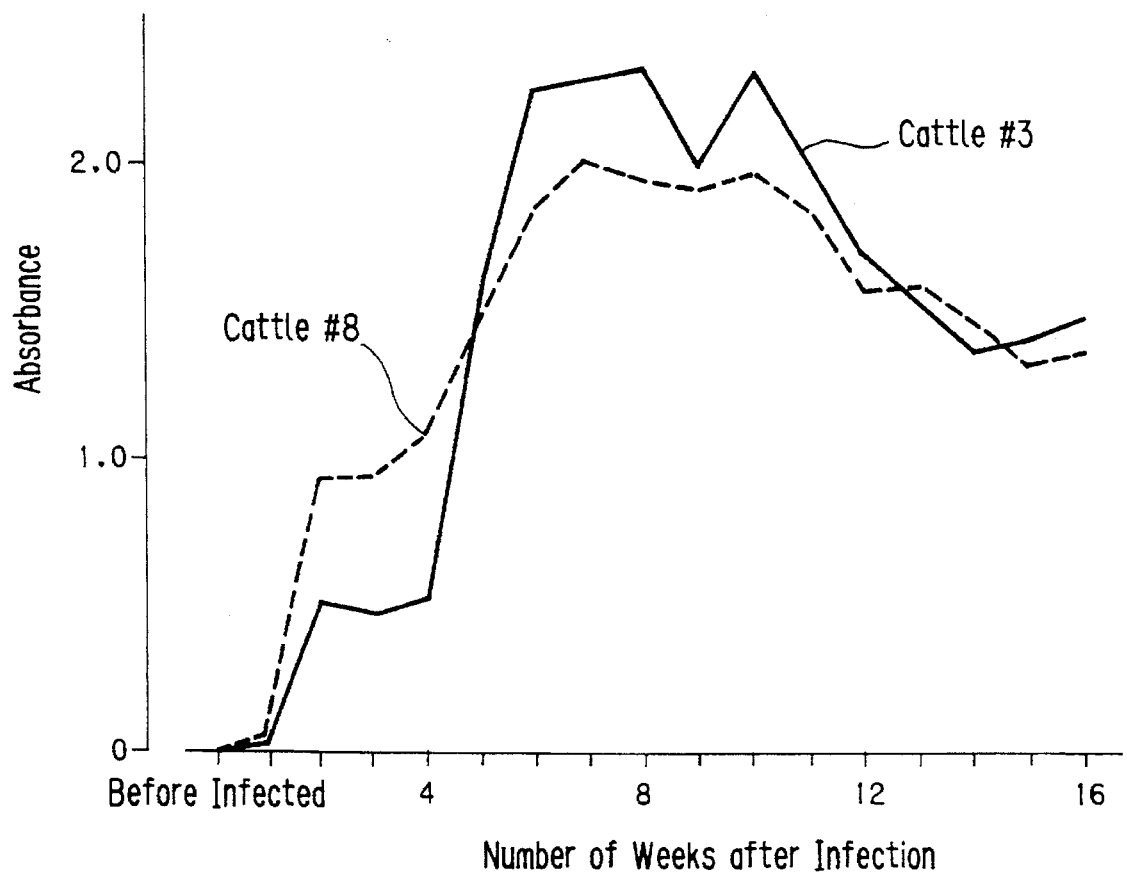
FIG. 3 shows the time-dependent variation in the antibody titers of FMD-infected cattle.

Using antigen A for diagnosis of FMD that had been prepared in the same manner as in Example 2, checked was the variation in the antibody titers of the sera as collected from FMD-infected cattle (#3 and #8) before the infection and up to 16 weeks after the infection, according to the above-mentioned indirect enzyme-linked immunosorbent assay method. The results obtained are shown in FIG. 3. Precisely, antigen A was applied to the 1:600 dilutions of the anti-sera collected from the cattle #3 and to the 1:100 dilutions of the anti-sera collected from the cattle #8.

For the both cattle, a significant increase in the antibody titer was noted 2 weeks after the infection while the high antibody titer was kept up to 16 weeks after the infection.

EXAMPLE 7

Figure 4:
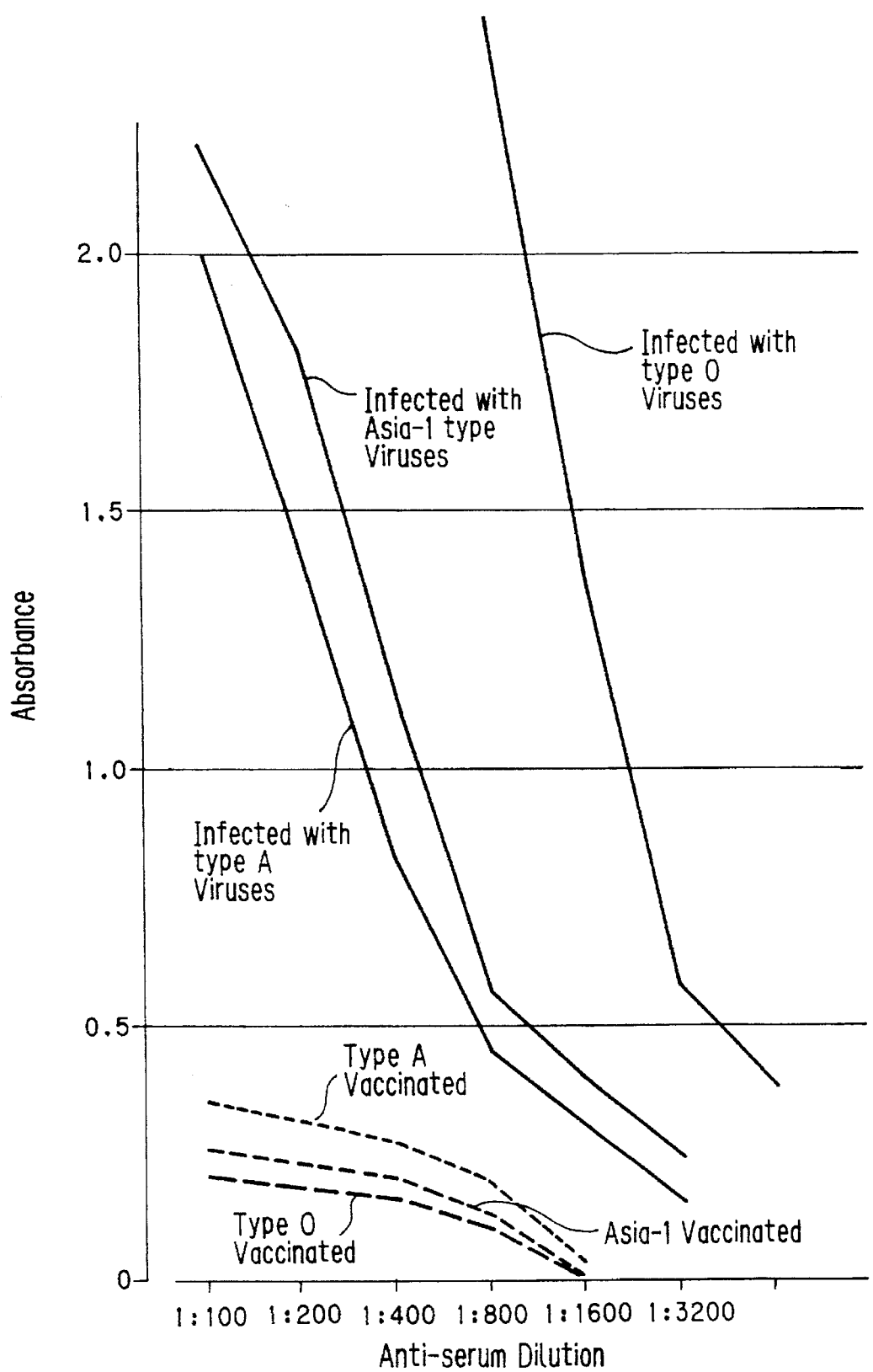
FIG. 4 shows the antibody tilers of FMD-infected cattle and those of vaccine-dosed cattle.

Antigen A for diagnosis of FMD that had been prepared in the same manner as in Example 2 was applied to the anti-sera as collected from cattle that had been experimentally infected with any of FMD O-type, A-type and Asia-1-type viruses and to the anti-sera as collected from cattle that had been inoculated with any of vaccines of the same three types (prepared in the Thailand FMD Vaccine Production Center), whereupon the antibody titer of each anti-serum was obtained according to the above-mentioned indirect ELISA method. The results obtained are shown in FIG. 4.

For vaccine-inoculated cattle, their anti-sets were collected 3 weeks after the inoculation as having the highest antibody titer. For experimentally infected cattle, their antisera were collected 9 weeks after the infection with O-type FMD viruses and 5 weeks or so after the infection with either A-type or Asia-1-type viruses.

For all the viral types, the antibody titer of every antiserum collected from the infected cattle was significantly higher than that of the corresponding anti-serum collected from the vaccinated cattle. It may be easily considered that, if more highly purified vaccines are used, the difference in the antibody titer between the infected cattle and the vaccinated ones will be greater.

From these results, it is believed that the present invention provides not only for FMD-free countries the technique of detecting FMD-specific antibodies for preventing them from being invaded by FMD but also for FMD-infected countries, where the current vaccines are used in order to reduce the regions with prevailing FMD and finally to eradicate FMD, an extremely effective technique of diagnosing FMD infection.

EXAMPLE 8

To about 0.01 mEq of a carboxylated polystyrene (product of Sigma in U.S.A.), added was 2 equivalent times of peptide A as obtained in Example 1. In addition, added thereto was 5 equivalent times of 1-ethyl-3-dimethylaminopropylcarbodiimide hydrochloride. Then, these were reacted at 4° C. for 24 hours. After the free peptide that had not been bonded to the latex particles was removed by washing, the bonded peptide was suspended in one ml of a phosphate buffer. The resulting suspension was diluted to 1:20. To 0.05 ml of the dilution, added was the same amount of the serum that had been collected from cattle (#4) 4 weeks after the infection with FMD and had been diluted to a varying degree, and these were reacted. As a result the reaction, the coagulation of the serum having a degree of dilution of 1:64 or higher was recognized within 30 minutes at room temperature. This suggests the possibility of simple diagnosis of EMD by the use of the peptide, though the sensitivity in this method is much lower than that in the indirect ELISA method.

EXAMPLE 9

Using other proteins (rabbit globulin, rabbit albumin, equine albumin, etc.) instead of equine globulin, various bonded peptides were obtained in the same manner as in Example 3. Like the equine globulin-bonded peptides, these were tested in the same manner. As a result, it was verified that all these bonded peptides are usable as antigens for diagnosis of FMD.

---

What is claimed is:

1. Peptide A, having the amino acid sequence of SEQ ID NO:1.

2. A diagnostic composition, comprising the peptide of claim 1 bonded to a carrier.

3. The diagnostic composition of claim 2, wherein the carrier is equine globulin or latex particles.

4. A method for detection of antibodies to foot and mouth disease (FMD) virus, comprising:

contacting a biological sample from an animal suspected of having said antibodies with the diagnostic composition of claim 2, and detecting specific binding of said antibodies to said diagnostic composition, wherein the presence of said specific binding indicates the presence of antibodies to FMD virus.

5. Peptide B, having the amino acid sequence of SEQ ID NO:2.

6. A diagnostic composition, comprising the peptide of claim 5 bonded to a carrier.

7. The diagnostic composition of claim 6, wherein the carrier is equine globulin or latex particles.

8. A method for detection of antibodies to FMD virus, comprising:

contacting a biological sample from an animal suspected of having said antibodies with the diagnostic composition of claim 6, and detecting specific binding of said antibodies to said diagnostic composition, wherein the presence of said specific binding indicates the presence of antibodies to FMD virus.

* * * * *